United States Patent

Katsurada et al.

[11] Patent Number: 5,868,663
[45] Date of Patent: Feb. 9, 1999

[54] FRONT END STRUCTURE OF SIDE-VIEW TYPE ENDOSCOPE

[75] Inventors: Hiroyuki Katsurada; Shinichi Matsuno, both of Tokyo, Japan

[73] Assignee: Asahi Kogaku Kogyo Kabushiki Kaisha, Tokyo, Japan

[21] Appl. No.: 823,075

[22] Filed: Mar. 24, 1997

[30] Foreign Application Priority Data

Mar. 26, 1996 [JP] Japan ................................ 8-069515
Mar. 27, 1996 [JP] Japan ................................ 8-071598
Jan. 16, 1997 [JP] Japan ................................ 9-005421

[51] Int. Cl.⁶ ........................................ A61B 1/00
[52] U.S. Cl. ................. 600/107; 600/106; 600/127; 600/129
[58] Field of Search ................... 600/104, 106, 600/107, 113, 121, 123, 127, 129, 128, 160, 170, 171

[56] References Cited

U.S. PATENT DOCUMENTS

| 4,841,949 | 6/1989 | Shimizu et al. | 600/107 |
| 5,562,600 | 10/1996 | Matsuno | 600/107 |
| 5,569,157 | 10/1996 | Nakazawa et al. | 600/106 X |

FOREIGN PATENT DOCUMENTS 62-6716   1/1987   Japan.
451764   12/1992   Japan.

Primary Examiner—Beverly M. Flanagan
Attorney, Agent, or Firm—Kane, Dalsimer, Sullivan, Kurucz, Levy, Eisele and Richard, LLP

[57] ABSTRACT

In a front end structure of a side-view type endoscope in which a treatment tool raising piece is swingably held in a raising piece receiving groove formed in the front end body, a bridge is provided on the front end surface of the front end body and extends to bridge a front opening of the raising piece receiving groove.

17 Claims, 11 Drawing Sheets

FRONT END STRUCTURE OF SIDE-VIEW TYPE ENDOSCOPE

BACKGROUND OF THE INVENTION

1. Field of the Invention

The present invention relates to the structure of the front end of a side-view type endoscope which is provided with a treatment tool raising portion provided in the front end of the body thereof.

2. Description of the Related Art

In general, an endoscope includes an insertion portion which can be inserted in a human body and which is provided with a treatment tool insertion channel. When a treatment tool is inserted in the insertion channel, the front end thereof projects from the front end of the insertion portion of the endoscope.

In case of a side-view type endoscope which is adapted to view the lateral portion of the front end of the insertion portion thereof, as can be seen in FIG. 11, the front end body 1 of the endoscope is provided with a treatment tool (instrument) raising portion (raising piece) 3 which raises the projecting front end of the treatment tool toward the lateral portion of the front end body 1, so that the front end of the treatment tool is located around the center portion of the field of view.

The raising piece 3 is held in a receptacle groove 2 formed in the front end body 1. The raising piece 3 is made of stainless steel and is rotatable about an axis 8. The receptacle groove 2 opens at the front end and the opposed side portions. The raising piece 3 can be swung by a remote-control operation so that the treatment tool 6 disposed on the raising piece 3 protrudes in the forward and upward (oblique) direction or the lateral direction. Note that 4 designates the view window, and 5 the illumination window, respectively.

To prevent the distal end of the front end body 1 from coming into direct contact with a mucous membrane in a body cavity of a patient, possibly doing harm to the mucous membrane, the front end body 1 of the endoscope is surrounded by an end cap 30 which is attached to the front end body 1 and is detachable.

The end cap 30 is made of an elastic material and is provided, on the inner peripheral surface near the rear end thereof, with a small diameter annular portion 32 which projects toward the center axis thereof. When the annular projection 32 is fitted in a peripheral groove 7 formed on the outer peripheral surface of the front end body 1, the end cap 30 is connected to the front end body 1.

There is a possibility that the end cap 30 may be completely or partially disengaged from the front end body 1 when the front end body forcedly passes through a strictured portion within a body cavity during an examination using the endoscope.

Consequently, acute angle portions 2a of the receptacle groove 2 that are located on the front end surface of the metal front end body 1 are exposed and may be pressed onto the mucous membrane during the insertion of the endoscope or a suction operation, possibly causing harm to the mucous membrane. The same occurs when an operator (doctor) fails to attach the end cap 30 to the front end body 1 by mistake.

It is an object of the present invention to provide a front end structure of an endoscope in which there is no possibility that a mucous membrane or the like is harmed by a front end portion of a receptacle groove which receives therein a raising piece even if the end cap is accidentally disengaged from the front end body of the endoscope, or no end cap is attached to the front end body by mistake.

SUMMARY OF THE INVENTION

To achieve the object mentioned above, according to the present invention, there is provided a front end structure of a side-view type endoscope comprising a metal front end body, a raising piece receiving groove being opened at the front end of the front end body, a treatment tool raising piece which is swingably held in said raising piece receiving groove, and a bridge which is provided on the front end surface of the front end body and which extends to bridge a front opening of the raising piece receiving groove.

Preferably, an end cap is provided which is detachably attached to the front end body to surround the same to thereby prevent the outer surface of the front end body from being exposed. The bridge bridges the front opening of the raising piece receiving groove within the end cap, and the bridge is located at the foremost portion of the front end body.

The bridge can be made of a piece separate from the front end body and is attached to the front end body, or can be formed integral with the front end body.

In an embodiment, the bridge covers a part of the front opening of the raising piece receiving groove and does not cover a part of the front opening.

The front end structure of the side-view type endoscope further comprises a recess formed by the bridge at the front end of the front end body, and a projection formed at the closed bottom of the end cap. The projection is engaged in the recess when the end cap is completely fitted to the front end body. An audible click indicates the proper engagement of the projection in the recess.

The present disclosure relates to subject matter contained in Japanese Patent Application Nos.8-69515 ( filed on Mar. 26, 1996 ), 8-71598 ( filed on Mar. 27, 1996 ) and 9-5421 ( filed on Jan. 16, 1997 ) which are expressly incorporated herein by reference in their entireties.

BRIEF DESCRIPTION OF THE DRAWINGS

The invention will be discussed below in detail with reference to the accompanying drawings, in which.

DESCRIPTION OF THE PREFERRED EMBODIMENT

Figure 1:
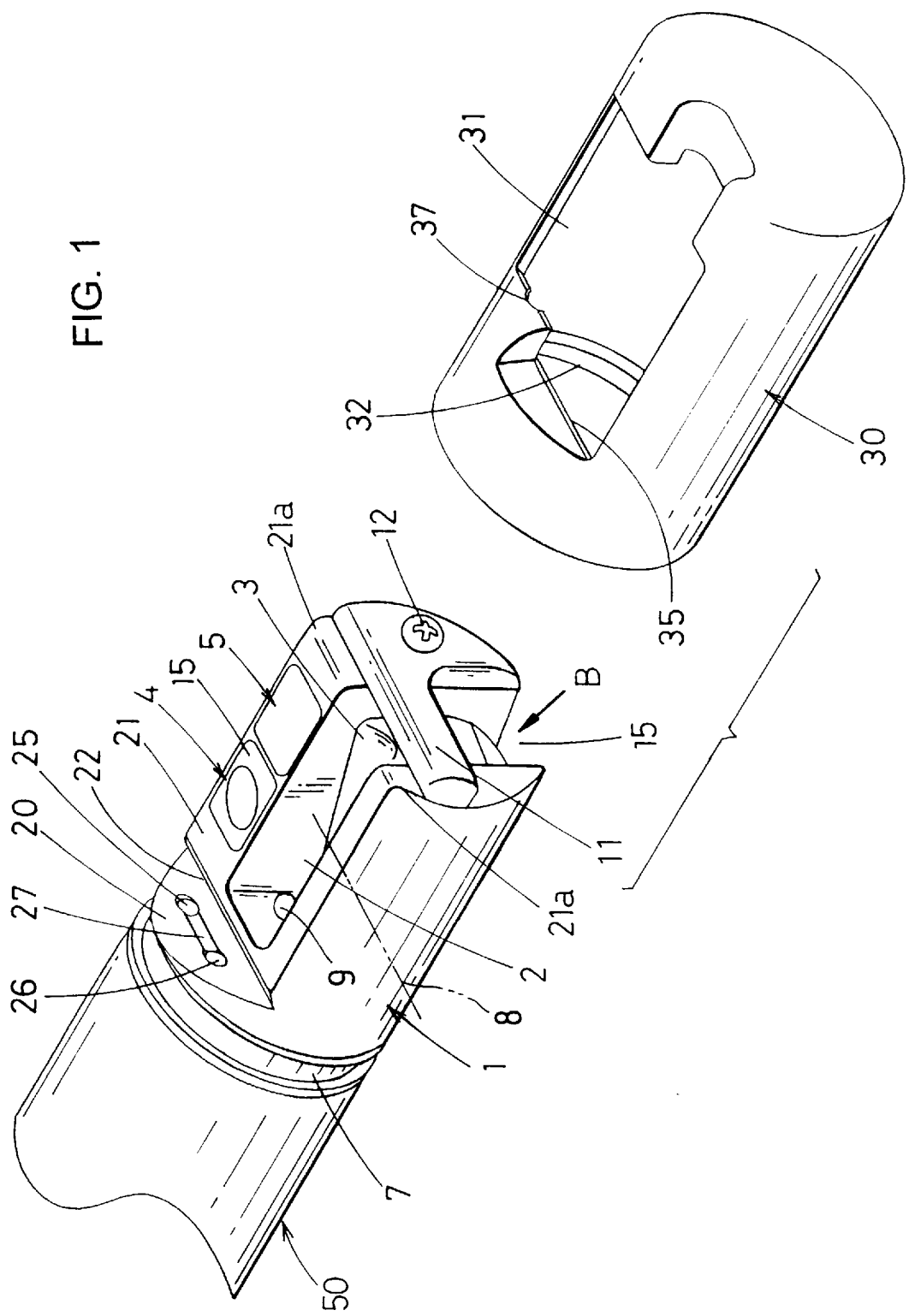
FIG. 1 is a perspective view of an embodiment of the present invention.

FIG. 1 shows a front end body 1 provided at the front end of an insertion portion of a side-view type endoscope, such as an endoscope for a duodenum, and an end cap 30 detached from the front end body 1. The front end body 1 is made of a corrosion-resistant metal such as stainless steel and is connected to the front end of a flexural portion 50 which can be bent by a remote control operation, and which is provided at the front end of an insertion portion of the endoscope.

The front end body 1 is in the form of a circular rod whose side surface is partially cut to form a flat surface (planar portion) 21 on which the view window 4 and the illumination window 5 are provided. The treatment tool raising piece receiving groove 2 is formed in the front end body 1 at the central portion thereof in the axial direction. The treatment tool raising piece 3 is received in the groove (receptacle groove) 2 to raise the front end of the treatment tool which projects from the front end body 1.

The receptacle groove 2 opens at the front end and the side surfaces thereof, so that the treatment tool can project from the front end of the front end body 1 in the upward and forward direction (oblique direction) or the lateral direction.

The front end body 1 is covered by an end cap 30 made of an elastic material, such as fluororubber, so that the portions of the front end body other than the view window 4, the illumination window 5 and the opening of the receptacle groove 2 adjacent to the planar portion 21 are not exposed.

The end cap 30 is in the form of a cylinder with a closed bottom, i.e., a cylinder having a closed front end and an open rear end. The end cap 30 is detachably attached to the front end body 1. The end cap 30 is provided with an opening 31 corresponding to the planar portion 21 of the front end body 1.

When the front end body 1 is inserted in the end cap 30, the latter is elastically expanded. When the end cap 30 is attached to the front end body 1, the annular projection 32, provided in the vicinity of the rear end of the end cap with an inner diameter slightly smaller than the inner diameter of the remaining portion of the end cap, is fitted in the peripheral groove 7 of the front end body 1 to prevent the end cap from being accidentally disengaged from the front end body 1.

The end cap 30 can be detached from the front end body 1 by expanding the rear end of the end cap and moving it in the direction opposite to the direction of the (sliding) movement when attaching the end cap to the front end body 1.

The treatment tool raising piece 3 has a uniform width (thickness) and is rotatably or swingably supported in the receptacle groove 2 to rotate about the shaft (axis) 8.

The raising piece 3 swings or rotates in the receptacle groove 2 about the shaft 8 through an operation wire (not shown) by a remote-control operation to change the direction of the front end of the treatment tool 60 which extends through a tool passage 9 (FIG. 2) and which projects from the front end body 1.

Figure 2:
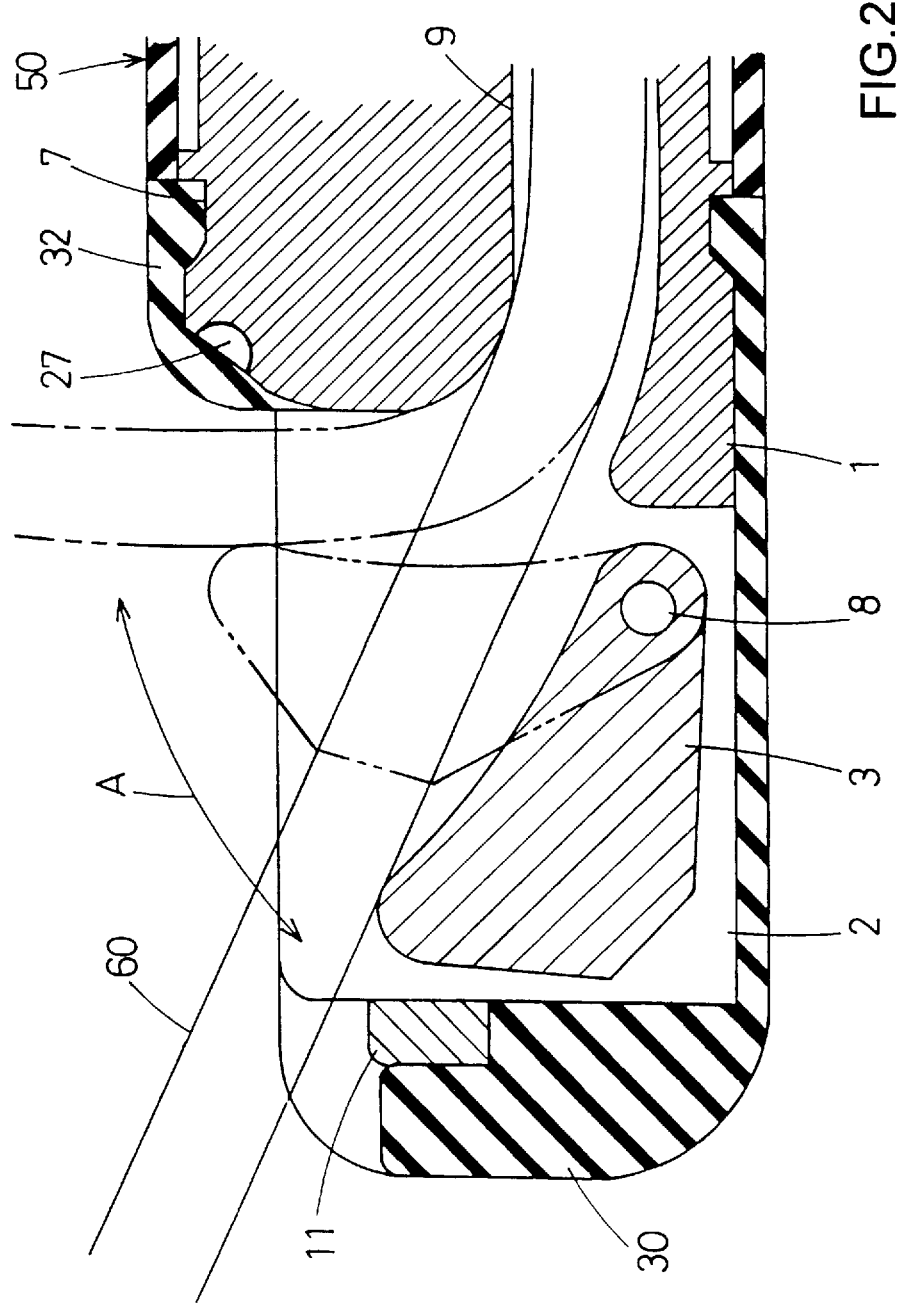
FIG. 2 is a sectional side view taken along a median plane of the raising piece receiving groove (receptacle groove) shown in FIG. 1.

To withdraw the front end of the treatment tool 60 outward from the receptacle groove 2, the raising piece 3 is moved to a lower position as indicated by a solid line in FIG. 2. In this state, the treatment tool 60 is moved in the forward and upward direction (oblique direction). Thereafter, in view of the side-view type endoscope in which the lateral side of the front end body 1 is to be viewed, the raising piece 3 is rotated to an upper position as indicated by an arrow "A" to orient the projecting front end of the treatment tool 60 in the lateral direction, so that the front end of the treatment tool 60 is located around the center of the field of view.

The planar portion 21 of the front end body 1 lies in conjugation with the rear end of the cover lens 15 of the view window 4. The planar portion 21 is provided on the rear end thereof with a V-shaped recessed groove 22 (as viewed from the lateral side) which extends over the entire width of the front end body 1.

The end cap 30 is provided with a downwardly protruding projection 35 which can be fitted in the recessed groove 22 of the front end body 1 in an air-tight fashion. Once the projection 35 is fitted in the recessed groove 22, no rotation of the end cap 30 relative to the front end body 1 takes place.

The planar portion (flat surface portion) 21 of the front end body 1 terminates at the recessed groove 22. The portion of the front end body 1 located behind the recessed groove 22 has a circular cross section. The surface of the front end body 1 that transfers from the deepest bottom portion of the recessed groove 22 to the circular cross section portion defines a tapered surface 20 which forms an obtuse angle more than 90 degrees with respect to the surface of the cover lens 15 and the planar portion 21. The tapered surface 20 is provided with openings, i.e., an air supply port 25 and a water supply port 26.

The air supply port 25 and the water supply port 26 are connected by means of an elongated connecting groove 27 which is laterally recessed in the tapered surface 20. Namely, the air supply port 25 and the water supply port 26 open into the connecting groove 27.

The end cap 30 is provided with a wall surface portion that partly covers the area of the planar portion 21 connected to the rear end of the view window 4. The wall surface portion of the end cap 30 in contact with the planar portion 21 is provided with a nozzle 37 which opens into the surface of the cover lens 15.

The rear opening of the nozzle 37 is directly connected to the connection groove 27. Thus, the air or water supplied from the air supply port 25 or the water supply port 26 is ejected from the nozzle 37 toward the surface of the cover lens 15 through the connecting groove 27.

The front end body 1 is provided on the front end surface thereof with a bridge 11 which extends across the opening of the receptacle groove 2 in the front end body 1. The bridge 11 is made of a piece separate from the front end body 1 and is secured to the front end body 1 by means of a screw 12.

Figure 3:
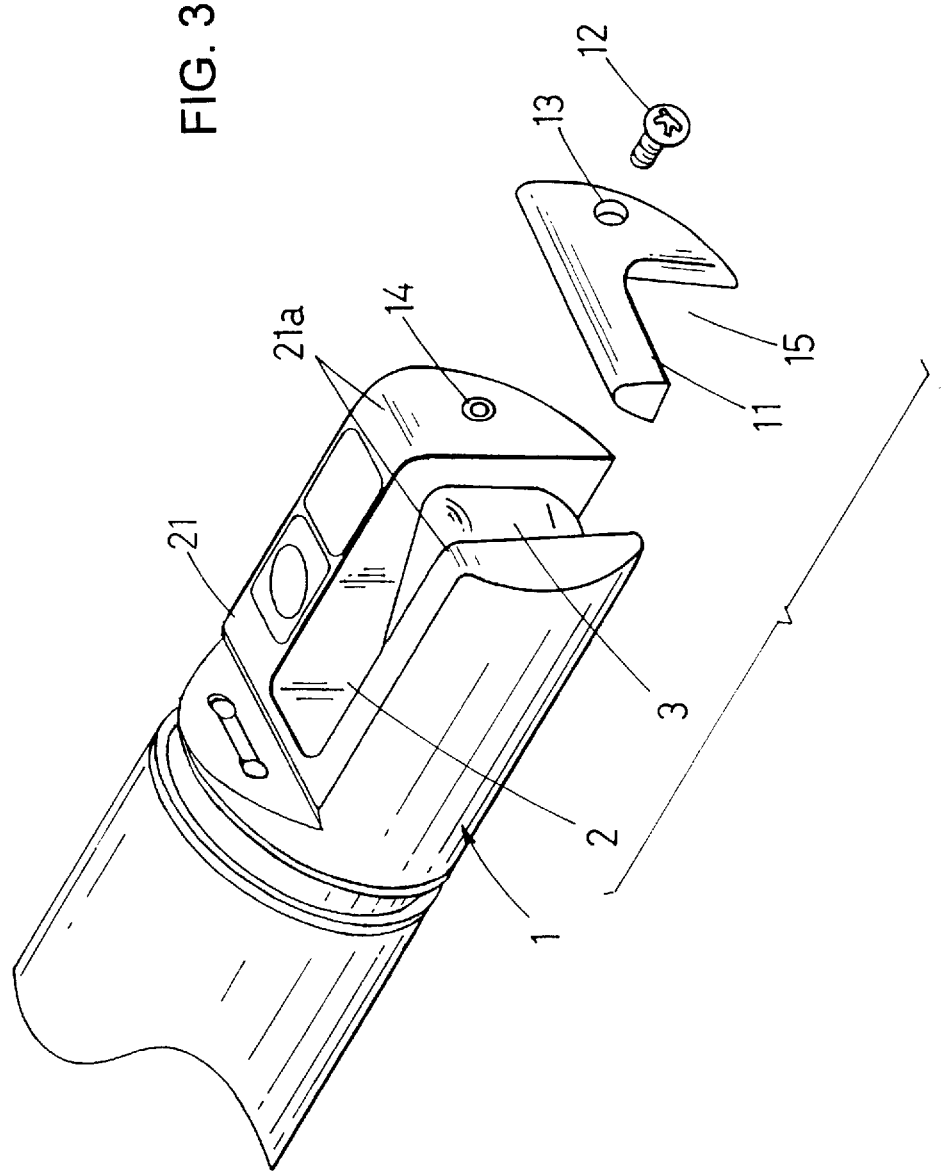
FIG. 3 is an exploded perspective view of the embodiment shown in FIG. 1.

FIG. 3 shows the bridge 11 detached from the front end body 1. The bridge 11 is provided with a hole 13 in which the screw 12 is inserted. The screw 12 is screwed into a threaded hole 14 formed in the front end surface of the front end body 1 through the hole 13 of the bridge 11 to secure the bridge 11 to the front end body 1.

The bridge 11 is provided with a cut-away portion 15 so as not to cover the lower half of the front end opening of the receptacle groove 2. The cut-away portion 15 makes it possible to insert a cleaning brush (not shown) in the receptacle groove 2 from the front end of the front end body 1 (in the direction "B" in FIG. 1) to thereby clean the receptacle groove 2 using the cleaning brush.

Figure 4:
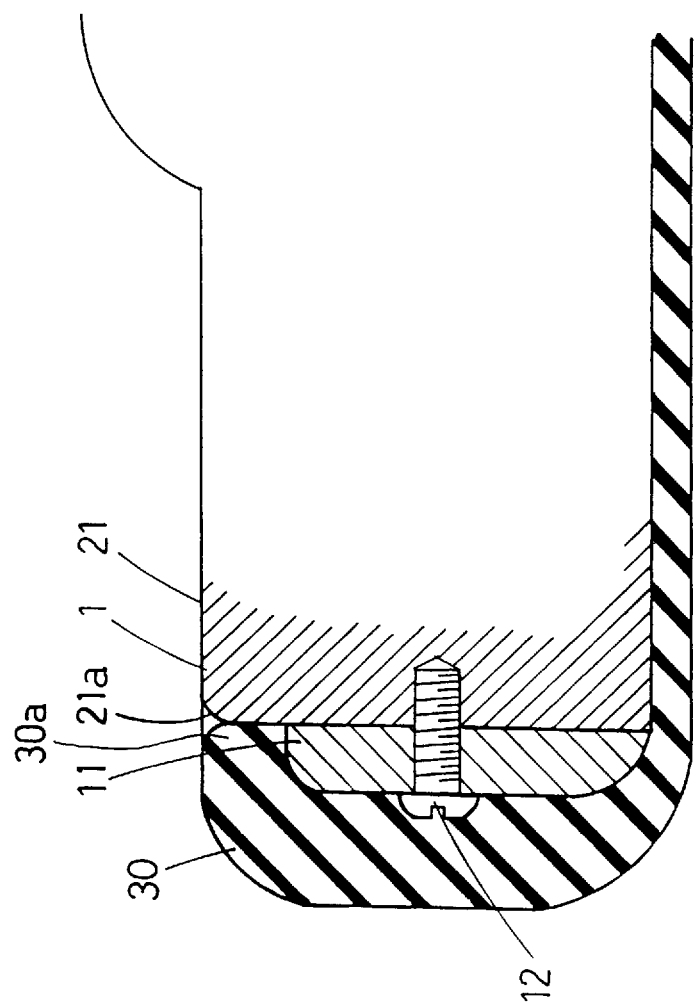
FIG. 4 is a sectional side view taken along a plane passing through the screw shown in FIG. 1.

The upper edge of the bridge 11 lies slightly lower than the flat surface 21 of the front end body 1 (e.g., by approximately 1 to 3 mm). As can be seen in FIG. 4 which is a sectional view taken along a plane passing through the screw 12, the bridge 11 is held between the upper and lower end portions of the end cap 30 at the front end of the front end body 1. With this arrangement, no displacement of the end cap 30 relative to the front end body 1 occurs. In other words, the end cap 30 is provided on the front end surface thereof with a projection 30a that projects toward the front end body 1 along the upper surface of the bridge 11.

The edges of the bridge 11 that could come into contact with a mucous membrane within a body cavity if the end cap 30 is detached from the front end body 1 are rounded. Alternatively, it is possible to chamfer the edges of the bridge 11 to define an obtuse angle. Moreover, the edge 21a of the planar surface 21 of the front end body 1, and other portions that appear over the bridge 11 are chamfered and rounded.

Consequently, if the end cap 30 is accidentally detached from the front end body 1, or the displacement of the end cap 30 relative to the front end body 1 occurs, only the bridge 11 or the rounded edges thereof or the rounded edge 21a of the planar portion 21 make contact with the mucous membrane. Hence, unlike the prior art, the front acute angle portion of the receptacle groove 2 and other acute angle portions are hardly brought into contact with the mucous membrane, which is free from harm during the insertion of the endoscope or suction operation.

Figure 5:
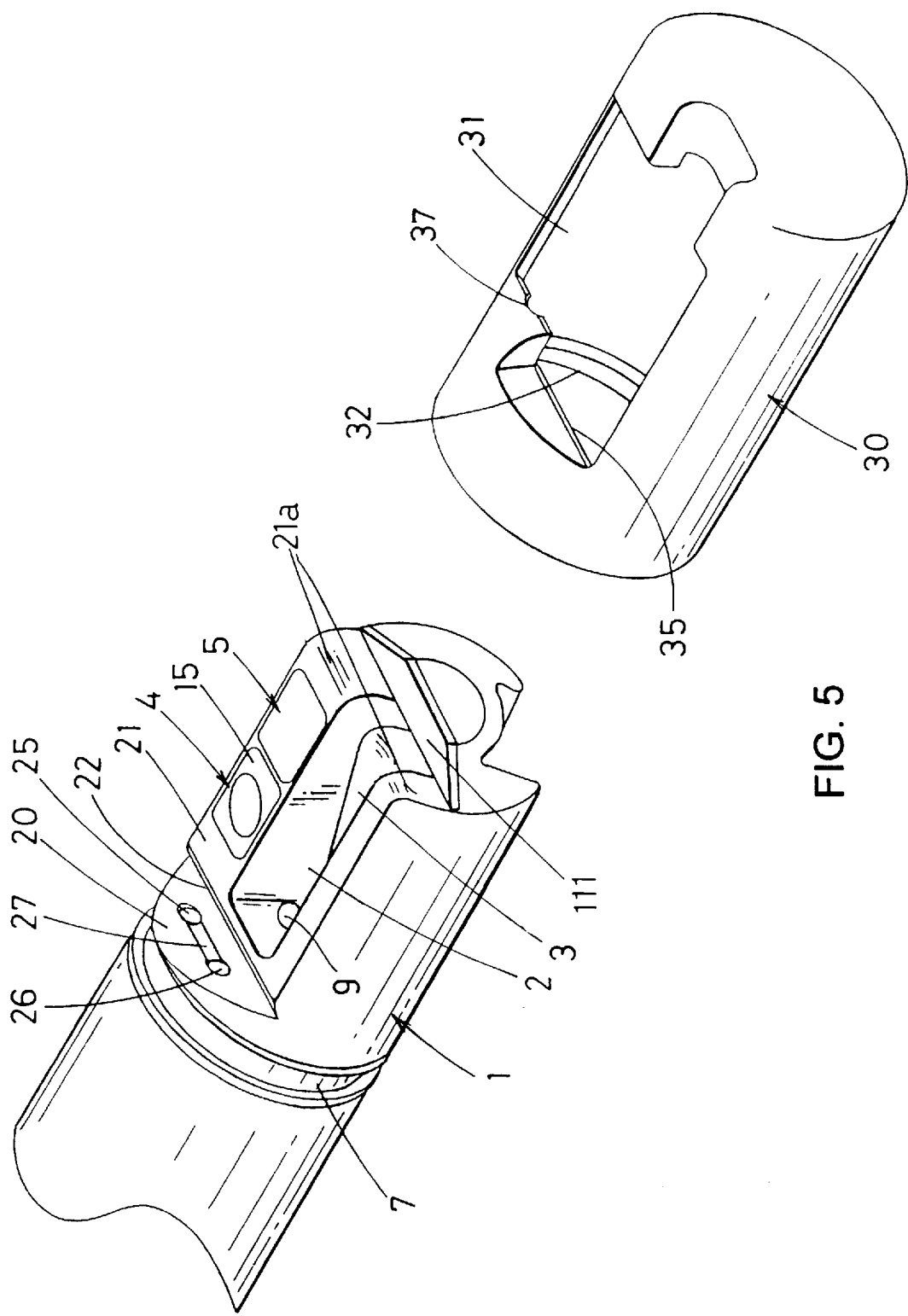
FIG. 5 is a perspective view of a second embodiment of the present invention.
Figure 6:
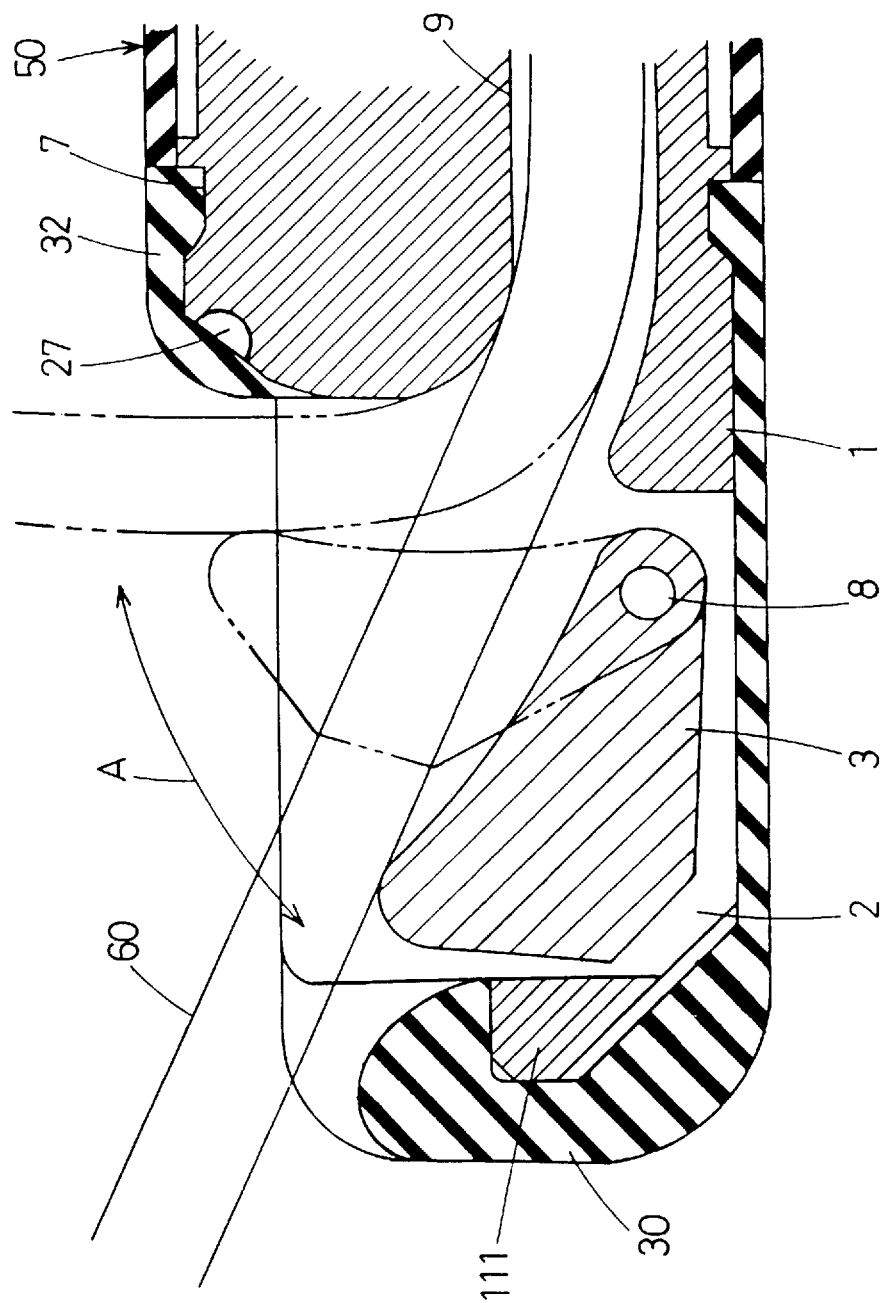
FIG. 6 is a sectional side view taken along a median plane of the raising piece receiving groove (receptacle groove) shown in FIG. 5.
Figure 7:
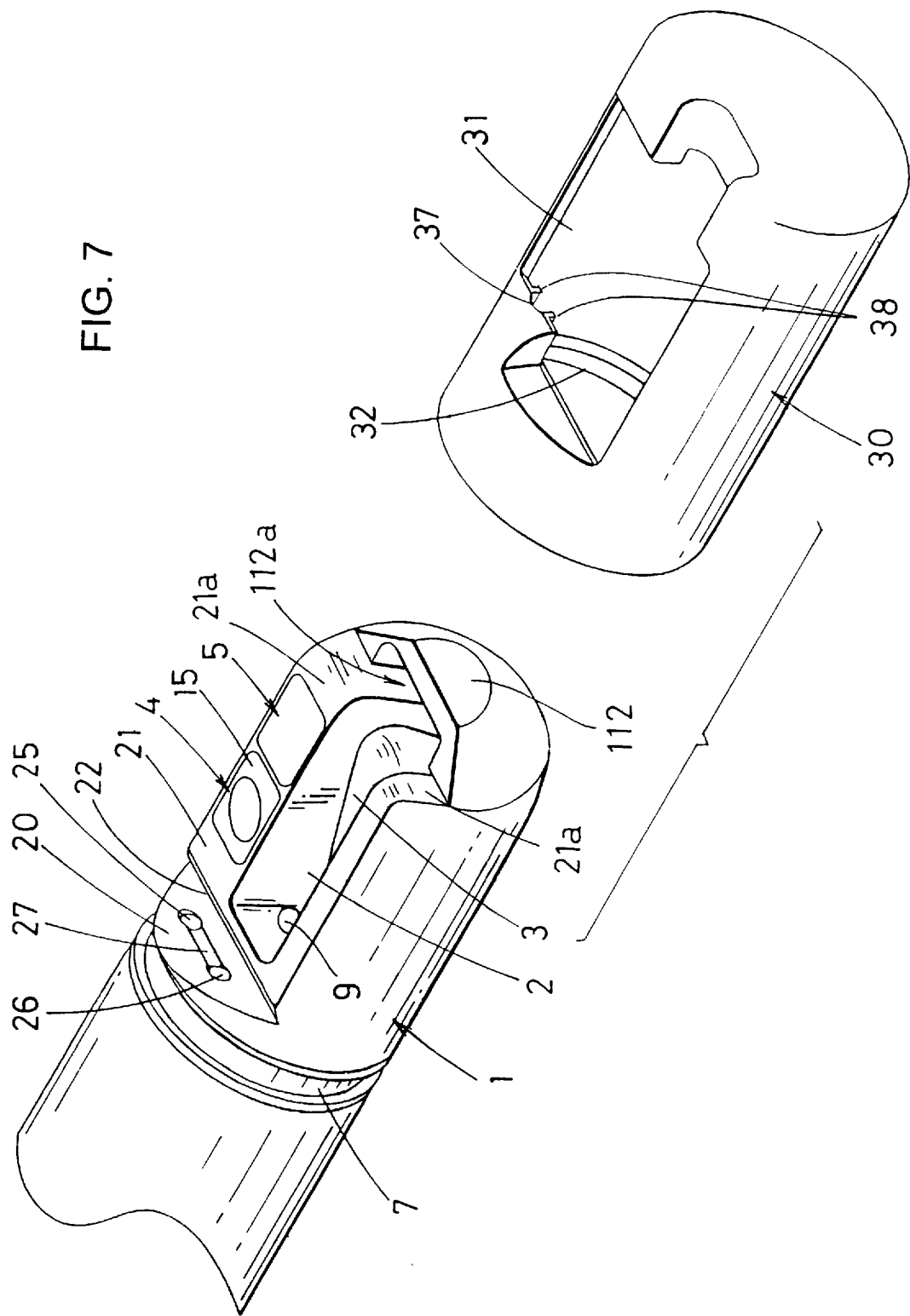
FIG. 7 is a perspective view of a third embodiment of the present invention, in which an end cap is detached from front end body of an endoscope.
Figure 8:
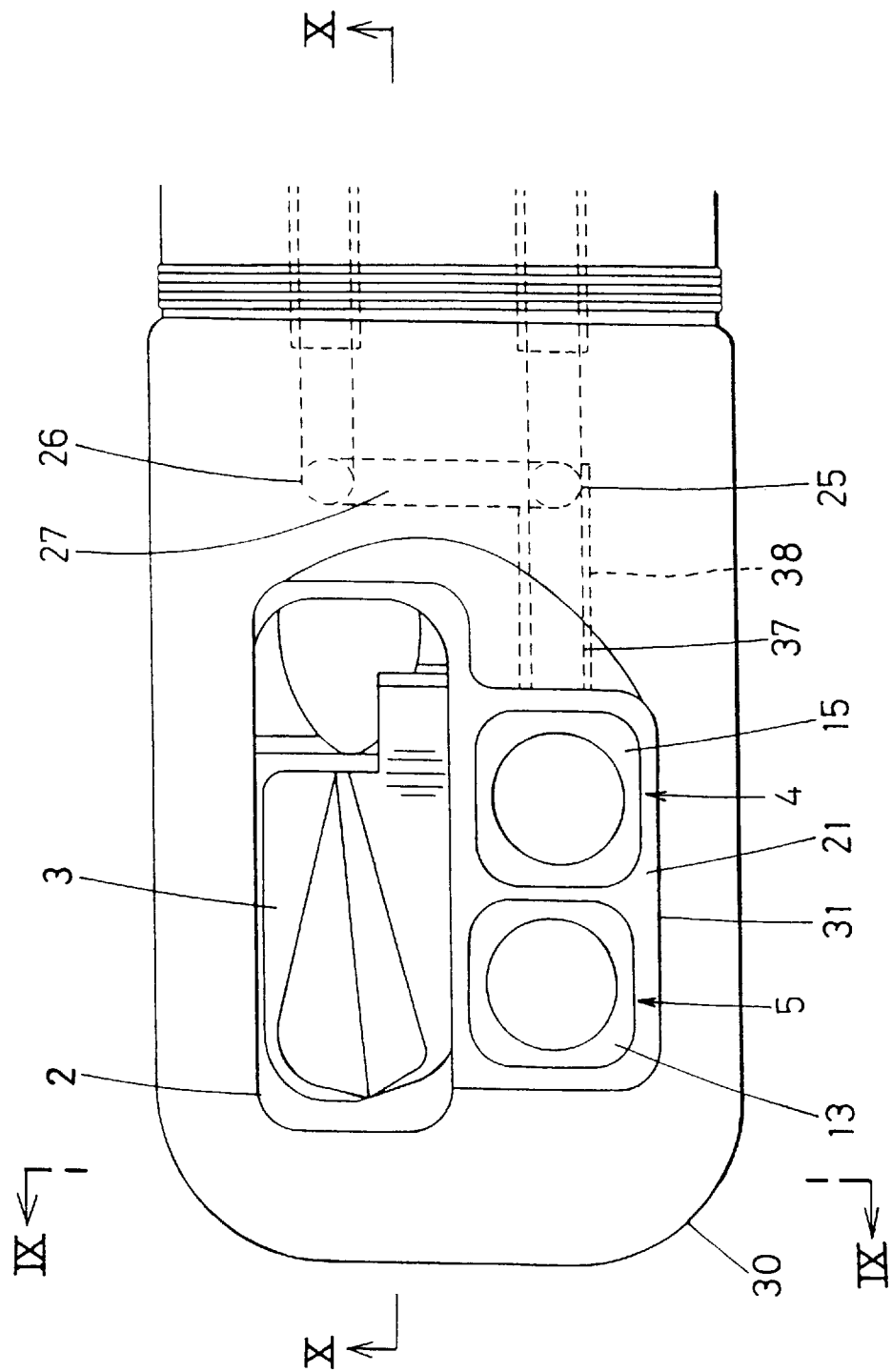
FIG. 8 is a plan view of FIG. 7, in which the end cap is attached to the front end body of the endoscope.
Figure 9:
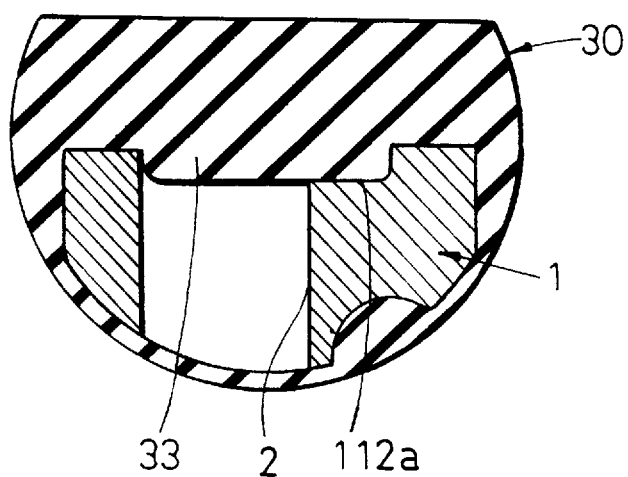
FIG. 9 is a sectional view taken along the line IX—IX in FIG. 8.
Figure 10:
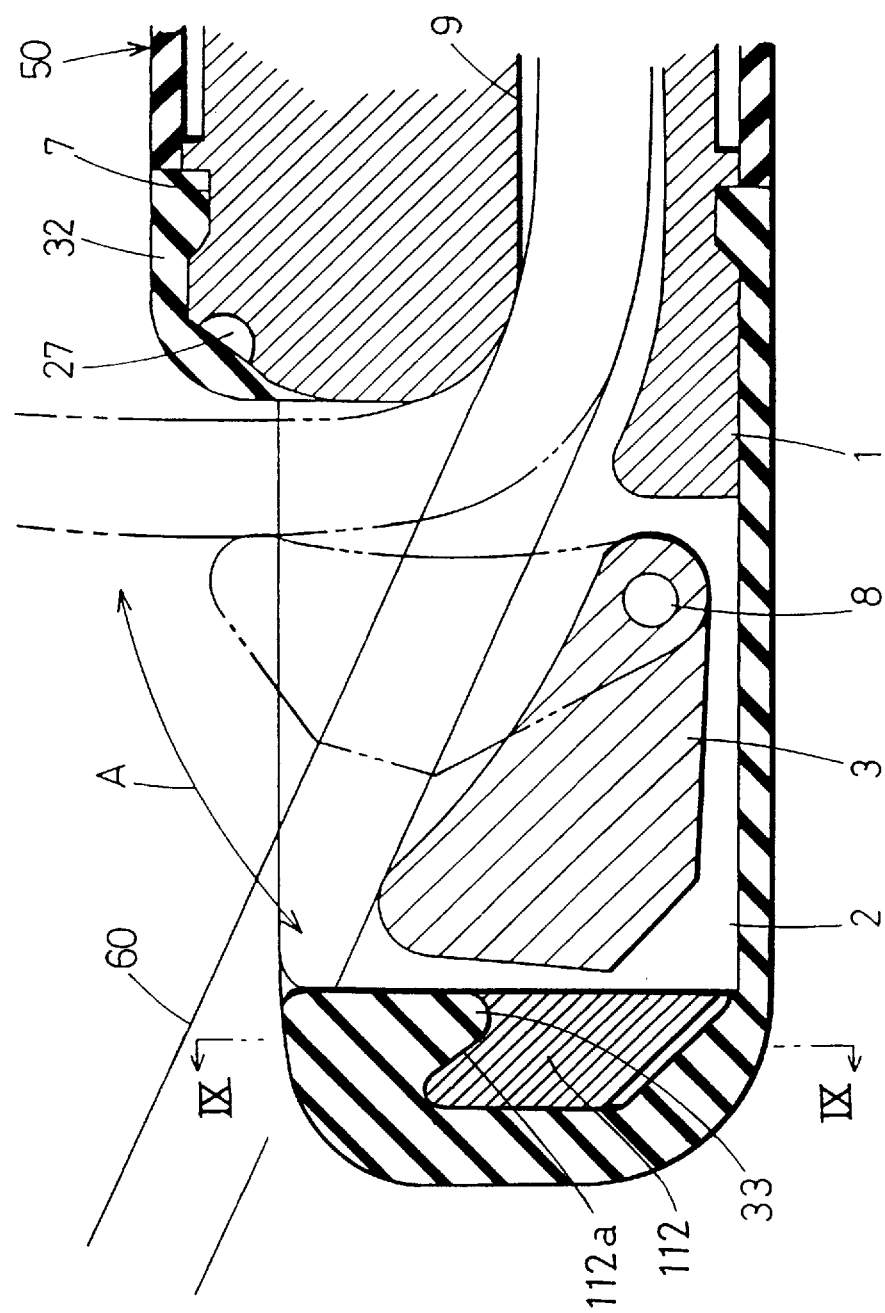
FIG. 10 is a sectional view taken along the line X—X in FIG. 8.
Figure 11:
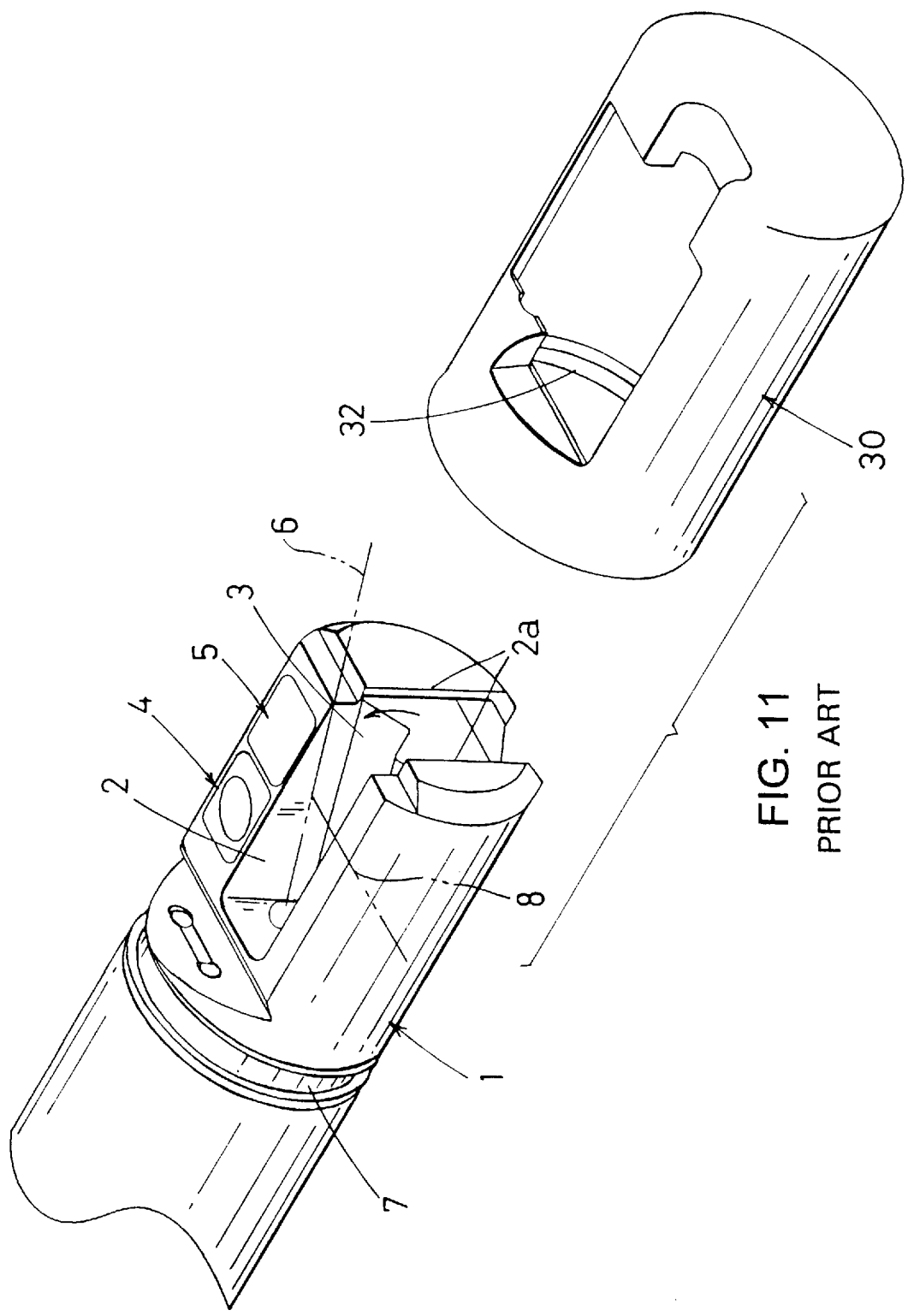
FIG. 11 is a perspective view of the front end portion of a known side-view type endoscope.

FIGS. 5 and 6 show a second embodiment of the present invention. In this embodiment, the bridge 111 is formed integral with front end body 1 and hence is made of stainless steel of which the front end body 1 is made. The integral formation of the bridge 111 and the front end body 1 contributes to a reduction in the number of elements and in the manufacturing cost. Moreover, the thin wall surface portion of the front end body 1 located outside the receptacle groove 2 tends not to deform, thus resulting in a smooth movement of the raising piece 3. Other structure of the second embodiment is the same as that of the first embodiment.

FIGS. 7 through 10 show a third embodiment of the present invention. The main differences between the third embodiment and the second embodiment are that 1) the bridge 112 integral with the front end body 1 is provided with a generally V-shaped pocket, or recess 112a, between the upper surface thereof and the front end surface of the front end body I and the end cap 30 is provided with a projection 33 which can be fitted in the recess 112a; 2) the bridge 112 is large enough to cover the lower half of the receptacle groove 2; 3) no groove 22 is provided on the rear end of the front end body 1, and hence the end cap 30 has no projection 35; and, 4) the end cap 30 is provided with projections 38 which extend along the lower surface of the nozzle 37 and which abut against the planar portion 21 of the front end body 1.

In the third embodiment, upon the attachment of the end cap 30 to the front end body 1, the projection 33 of the end cap 30 abuts against the front end surface of the front end body 1 and is fitted in the recess 112a immediately before the end cap 30 is completely fitted to the front end body 1. Consequently, it is necessary to deform and move the projection 33 upward by the application of a stronger force to thereby ride over the bank portion provided in front of the recess 112a. Thus, in order to correctly attach or engage the end cap 30 to or with the front end body 1, a click must be heard when the projection 33 is fitted in the recess 112a. The operator can confirm proper engagement by listening for the click.

As can be understood from the above discussion, according to the present invention, since the bridge which extends across the front opening of the raising piece receiving groove in the cap is provided on the front end surface of the front end body, there is no fear that the mucous membrane or the like is hurt by the front edge of the raising piece receiving groove if the end cap is accidentally detached from the front end body or the end cap is not firmly connected to the front end body. Thus, a highly safe endoscope can be provided.

What is claimed is:

1. A front end structure of a side-view type endoscope comprising:

a metal front end body;

a raising piece receiving groove formed in said front end body, a front end of said raising piece receiving groove being opened at a front end of said front end body;

a treatment tool raising piece which is swingably held in said raising piece receiving groove; and a bridge which is provided on the front end surface of the front end body and which extends to bridge said front opening of the raising piece receiving groove;

wherein said bridge covers a part of the front opening of said raising piece receiving groove and does not cover the remainder of the front opening.

2. The front end structure of a side-view endoscope according to claim 1, further comprising an end cap which is detachably attached to said front end body to surround the same to thereby prevent the outer surface of the front end body from being exposed.

3. The front end structure of a side-view endoscope according to claim 1, wherein said bridge is located at the foremost portion of the front end body.

4. The front end structure of a side-view endoscope according to claim 1, wherein said bridge is made of a piece separate from said front end body and is attached to the front end body.

5. The front end structure of a side-view endoscope according to claim 1, wherein said bridge is formed integral with said front end body.

6. A front end structure of a side-view endoscope comprising:

a metal front end body;

a raising piece receiving groove formed in said front end body, a front end of said raising piece receiving groove being opened at a front end of said front end body;

a treatment tool raising piece which is swingably held in said raising piece receiving groove; and a bridge which is provided on the front end surface of the front end body and which extends to bridge said front opening of the raising piece receiving groove;

wherein the edge of the outer surface of the bridge defines an obtuse angle.

7. The front end structure of a side-view endoscope according to claim 6, further comprising an end cap which is detachably attached to said front end of body to surround the same to thereby prevent the outer surface of the front end body from being exposed.

8. The front end structure of a side-view endoscope according to claim 6, wherein said bridge is located at the foremost portion of the front end body.

9. The front end structure of a side-view endoscope according to claim 6, wherein said bridge is made of a piece separate from said front end body and is attached to the front end body.

10. The front end structure of a side-view endoscope according to claim 6, wherein said bridge is formed integral with said front end body.

11. A front end structure of a side-view endoscope comprising:

a metal front end body;

a raising piece receiving groove formed in said front end body, a front end of said raising piece receiving groove being opened at a front end of said front end body;

a treatment tool raising piece which is swingably held in said raising piece receiving groove; and a bridge which is provided on the front end surface of the front end body and which extends to bridge said front opening of the raising piece receiving groove;

wherein the edge of the outer surface of the bridge is chamfered and rounded.

12. The front end structure of a side-view endoscope according to claim 11, further comprising an end cap which is detachably attached to said front end body to surround the same to thereby prevent the outer surface of the front end body from being exposed.

13. The front end structure of a side-view endoscope according to claim 11, wherein the bridge is located at the foremost portion of the front end body.

14. The front end structure of a side-view endoscope according to claim 11, wherein said bridge is made of a piece separate from said front end body and is attached to the front end body.

15. The front end structure of a side-view endoscope according to claim 11, wherein said bridge is formed integral with said front end body.

16. A front end structure of a side-view type endoscope comprising:

a metal front end body;

a raising piece receiving groove formed in said front end body, a front end of said raising piece receiving groove being opened at front end of said front end body;

a treatment tool raising piece which is swingably held in said raising piece receiving groove;

a bridge which is provided on the front end surface of the front end body and which extends to bridge said front opening of said raising piece receiving groove;

a recess formed by said bridge at the front end of said front end body an end cap in a form of a cylinder with a closed bottom, said end cap being detachably attached to the front end body to surround the same to thereby prevent the outer surface of the front end body from being exposed; and a projection formed at said closed bottom of the end cap, said projection being engaged in said recess when the cap is completely fitted to the front end body.

17. The front end structure of a side-view endoscope according to claim 16, wherein said recess and said projection are formed such that a click is heard when the projection is engaged in the recess.

* * * * *